(12) United States Patent
Hansen (10) Patent No.: US 8,158,910 B2
(45) Date of Patent: Apr. 17, 2012

(54) MEMORY TRANSFER DEVICE

(75) Inventor: William J. Hansen, Pewaukee, WI (US)

(73) Assignee: Enthermics Medical Systems, Inc., Menomonee Falls, WI (US)

(*) Notice: Subject to any disclaimer, the term of this patent is extended or adjusted under 35 U.S.C. 154(b) by 147 days.

(21) Appl. No.: 12/343,162

(22) Filed: Dec. 23, 2008

(65) Prior Publication Data
US 2009/0166349 A1    Jul. 2, 2009

Related U.S. Application Data

(63) Continuation of application No. 12/250,281, filed on Oct. 13, 2008.

(60) Provisional application No. 61/018,372, filed on Dec. 31, 2007.

(51) Int. Cl.
*A61F 7/00* (2006.01)
*A61B 19/00* (2006.01)
*F27D 19/00* (2006.01)

(52) U.S. Cl. ......... 219/385; 219/218; 219/412; 604/114

(58) Field of Classification Search ........................... None
See application file for complete search history.

(56) References Cited

U.S. PATENT DOCUMENTS

| | | | |
|---|---|---|---|
| 5,726,424 A * | 3/1998 | Koether | 219/414 |
| 5,864,120 A * | 1/1999 | Vroom et al. | 219/400 |
| 6,196,113 B1 | 3/2001 | Yung | |
| 6,294,762 B1 | 9/2001 | Faries et al. | |
| 6,467,953 B1 | 10/2002 | Faries et al. | |
| 6,566,631 B2 | 5/2003 | Faries et al. | |
| 6,660,974 B2 | 12/2003 | Faries et al. | |
| 6,762,930 B2 * | 7/2004 | Minne' | 361/679.55 |
| 6,768,085 B2 | 7/2004 | Faries et al. | |
| 7,041,941 B2 | 5/2006 | Faries et al. | |
| 7,276,675 B2 | 10/2007 | Faries et al. | |
| 7,307,245 B2 * | 12/2007 | Faries et al. | 219/413 |
| 7,364,657 B2 * | 4/2008 | Mandrusov et al. | 210/252 |
| 2001/0042743 A1 | 11/2001 | Faries et al. | |
| 2002/0021741 A1 | 2/2002 | Faries et al. | |
| 2002/0024990 A1 | 2/2002 | Faries et al. | |
| 2002/0034212 A1 | 3/2002 | Faries et al. | |
| 2002/0065685 A1 | 5/2002 | Sasaki et al. | |
| 2002/0158058 A1 | 10/2002 | Faries et al. | |

(Continued)

FOREIGN PATENT DOCUMENTS

DE    1182734    12/1964

(Continued)

OTHER PUBLICATIONS

Non-final Office action for related application U.S. Appl. No. 11/250,281 mailed Nov. 11, 2010, 12 pages.

*Primary Examiner* — Joseph M Pelham
(74) *Attorney, Agent, or Firm* — Boyle Fredrickson, S.C.

(57) ABSTRACT

A medical warming cabinet and a method of installing a controller into a medical warming cabinet is disclosed that allows for easy transfer of operation parameters between controllers. Should a controller fail, the removable memory device can be removed from the failed controller and inserted into the replacement controller. This provides the benefits of a generic controller (e.g., low cost and good availability), but eliminates the tedious and costly necessity of having to reprogram the controller during maintenance.

21 Claims, 4 Drawing Sheets

U.S. PATENT DOCUMENTS

| | | |
|---|---|---|
| 2003/0000939 A1 | 1/2003 | Faries et al. |
| 2003/0030731 A1 | 2/2003 | Colby |
| 2004/0170409 A1* | 9/2004 | Faries et al. .................. 392/470 |
| 2004/0188409 A1 | 9/2004 | Faries et al. |
| 2004/0240520 A1 | 12/2004 | Faries et al. |
| 2004/0247016 A1 | 12/2004 | Faries et al. |
| 2005/0240689 A1 | 10/2005 | Leaming |
| 2006/0291533 A1 | 12/2006 | Faries et al. |
| 2007/0000910 A1 | 1/2007 | Faries et al. |
| 2007/0015975 A1 | 1/2007 | Faries et al. |
| 2007/0093786 A1 | 4/2007 | Goldsmith et al. |
| 2007/0115808 A1 | 5/2007 | Ying |
| 2007/0142773 A1* | 6/2007 | Rosiello et al. ............... 604/113 |
| 2007/0155424 A1 | 7/2007 | Gasper et al. |
| 2008/0205481 A1* | 8/2008 | Faries et al. .................. 374/138 |

FOREIGN PATENT DOCUMENTS

| | | |
|---|---|---|
| DE | 3311805 | 10/1984 |
| DE | 4019395 | 12/1991 |
| DE | 10058412 | 6/2002 |
| DE | 10 2004 007227 A1 | 9/2005 |
| EP | 1182734 A2 | 2/2002 |

* cited by examiner

MEMORY TRANSFER DEVICE

CROSS-REFERENCE TO RELATED APPLICATIONS

This application claims the benefit of U.S. provisional patent application Ser. No. 61/018,372 entitled "CONTROLLER FOR MEDICAL WARMING CABINETS" filed on Dec. 31, 2007 and is a continuation of U.S. patent application Ser. No. 12/250,281 entitled "DATA LOGGER" filed on Oct. 13, 2008. The contents of both of these applications is hereby incorporated by reference as if set forth in their entirety herein.

STATEMENT REGARDING FEDERALLY SPONSORED RESEARCH

Not applicable.

BACKGROUND OF THE INVENTION

This invention is directed at medical warming cabinets. In particular, this invention is directed at the programming of a controller for a medical warming cabinet.

Medical warming cabinets may be used to warm blankets, fluids, and the like. Medical warming cabinets must operate under the proper temperatures and parameters to avoid overheating and/or spoilage of the items being heated. To this end, the controllers are often programmed to keep each of the heating compartments within a particular temperature range and to alert the user if there has been non-compliance with the desired heating treatment. In some cases, the end user may be restricted altogether from operating outside of defined operational parameters.

Often, the controller installed in the medical warming cabinet is a generic controller suitable for use in any one of a number of models. During commissioning, this generic controller is programmed by a skilled technician for the particular cabinet and/or for a particular set of operating parameters. Although the programming of the generic controller is a long and tedious task, the overall cost of a programmed generic controller is typically less than the cost of manufacturing a controller that is unique to a specific medical warming cabinet.

During the operation life of the medical warming cabinet, some of the components may fail. Most frequently, the failure is not systemic, but rather involves the mechanical failure of a particular component or sub-component. For example, a display screen or user input switch on the controller may fail. However, these types of failures necessitate replacing the entire controller.

Unfortunately, the replacement of even small broken components require reprogramming the new controller. Given that the service technician may service a number of different models and that even a single incorrect button push may result in improper operation of the cabinet, such reprogramming is particularly error prone. Further, the technician may not have a record of the original operational parameters on hand while reprogramming the cabinet. If the controller is improperly programmed, then an additional service call may be required in order to restore the cabinet to service.

Hence, there is a need for an improved controller for a medical warming cabinet that is both generic in form and that is easily replaceable. In particular, there is a need for a controller that is less susceptible to programming errors upon replacement of the controller.

BRIEF SUMMARY OF THE INVENTION

A medical warming cabinet is disclosed. The medical warming cabinet includes a compartment, a heating apparatus for warming the compartment, and a controller configured to operate the heating apparatus. The controller includes a removable memory device connector for receiving a removable memory device. The medical warming cabinet further includes a removable memory device removably received in the removable memory device connector. The removable memory device contains information related to the operational parameters of the medical warming cabinet. The controller, and hence the entire medical warming cabinet, operates according to operational parameters stored on the removable memory device.

In one form, the controller may include user inputs for altering the information stored on the removable memory device.

In another form, the medical warming cabinet may also include a data logging module for sampling, storing, and reporting operational data.

In yet another form, the medical warming cabinet may include at least a first compartment having a first heating apparatus and a second compartment having a second heating apparatus. The removable memory device may contain separate operational parameters for the first compartment and the second compartment.

In still yet another form, the information on the removable memory device may include heating control algorithm information.

In another form, the removable memory device may include different operational parameters for different items to be warmed. The controller may have individual temperature controls for irrigation fluids and injection fluids.

A method of installing a controller into a medical warming cabinet is also disclosed. The method includes providing a controller having a memory device connector and a connector for connecting the controller to a heating apparatus. A removable memory device containing information related to the operational parameters of the medical warming cabinet is also provided. The removable memory device is inserted into the memory device connector on the controller. The controller is installed into the medical warming cabinet. The information on the removable memory device is read by the controller upon operation and the medical warming cabinet operates according to the information stored on the removable memory device.

In one form, the method may further include the step of operating user inputs on the controller to alter the information stored on the removable memory device.

In another form, the method may further include sampling operational data using the controller and storing the operational data on a portion of the removable memory device.

In yet another form, the medical warming cabinet may include at least a first compartment having a first heating apparatus and a second compartment having a second heating apparatus. In this form, the information related to operational parameters of the medical warming cabinet may include separate operational parameters for the first compartment and the second compartment.

In still yet another form, the information may include heating control algorithm information.

In another form, the removable memory device may include different operational parameters for different items to be warmed.

In yet another form, the controller may have individual temperature controls for irrigation fluids and injection fluids.

Thus, a medical warming cabinet and a method of installing a controller into a medical warming cabinet is disclosed that allows for easy transfer of operation parameters between controllers. Should a controller fail, the removable memory device can be removed from the failed controller and inserted into the replacement controller. This provides the benefits of a generic controller (e.g., low cost and good availability), but eliminates the tedious and costly necessity of having to reprogram the controller during maintenance.

These and still other advantages of the invention will be apparent from the detailed description and drawings. What follows is merely a description of some preferred embodiments of the present invention. To assess the full scope of the invention the claims should be looked to as these preferred embodiments are not intended to be the only embodiments within the scope of the claims.

DETAILED DESCRIPTION OF THE PREFERRED EMBODIMENTS

Figure 1:
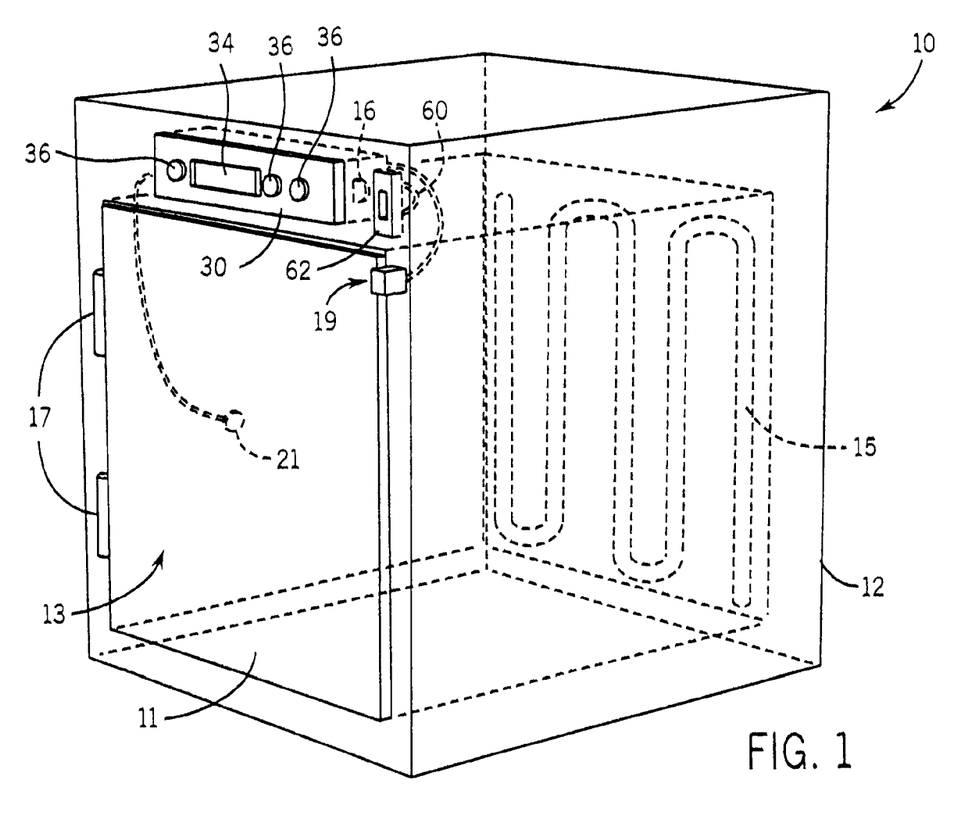
FIG. 1 is a perspective view of a medical warming cabinet with a controller including a removable memory device.

Referring now to FIG. 1, a medical warming cabinet 10 includes a door 11 and walls 12 that define a compartment or heating chamber 13. The heating chamber 13 receives and warms medical items, such as blankets, fluids, and the like.

The door 11 provides access to the heating chamber 13. As shown, the door 11 is hinged to the walls 12 by hinges 17. A door sensor 19 is present that detects whether the door 11 is open or shut. The door sensor 19 may be any kind of sensor including, but not limited to, a mechanical button, switch, or lever that is depressed when the door 11 is closed, an optical sensor, an electrical sensor, a magnetic sensor, and the like.

A heating apparatus 15 heats the heating chamber 13 and is connected to and controlled by a controller 30. The heating apparatus 15 can be a heating element, with or without a heat circulating fan, or a low-heat-density electrothermal cable or pad array that is mounted against the inside or outside of the walls 12 define the chamber 13.

The controller 30 is configured to operate the heating apparatus 15 at a particular temperature selected by a user. The controller 30 includes a plurality of user inputs 36 and a display 34. The controller 30 is connected to the door sensor 19 and a temperature sensor 21 for measuring the temperature of the heating chamber 13. Although the temperature sensor 21 is shown as being placed on a side wall of the heating chamber 13, it may be placed in any one of a number of positions within the heating chamber 13. Furthermore, the medical warming cabinet 10 can include an alarm that indicates when a temperature exceeds a temperature that is a certain amount higher than the set temperature.

A removable memory device 16 is removably received in the controller 30. Preferably, the removable memory device 16 is not accessible without first disassembling the medical warming cabinet 10.

The removable memory device 16 includes information related to the operation of the cabinet 10. The information can be stored in a configuration file format. The information can include software versions and heating control algorithm information such as allowable temperature ranges and proportional-integral-derivative controller (PID controller) parameters. Depending on the particular application, the information in the configuration file stored on the removable memory device 16 can include, but is not limited to, the type of warmer, the model number, the serial number, the year of manufacturing, the month of manufacturing, the date of manufacturing, the type of warmer (i.e., blanket or fluid), the injection fluids warming minimum temperature, the injection fluids maximum temperature, the irrigation fluids minimum temperature, the irrigation fluids maximum temperature, the blanket minimum temperature, the blanket maximum temperature, PID integration compensation term normalized to 150 degrees F., PID "D" term normalized to 150 degrees F., PID "I" term normalized to 150 degrees F., PID "P" term normalized to 150 degrees F.; PID "D" sampling period in half seconds, check door sensor enable, the frequency of any data collection module, the number of temperature sensors, the output type (e.g., solid state relay or mechanical relay), and control limits for the relay on each side of the setpoint. The temperature parameters can be stored in Fahrenheit, Celsius, Kelvin, or any other scale.

For fluid warming cabinets, the controller 30 can be configured to allow for individual temperature controls for irrigation fluids (IRR) and injection fluids (INJ). For example, the IRR temperature can be adjusted within a first range and the INJ temperature can be set within a second range, which is typically lower than the IRR range. The appropriate range of temperatures is available automatically once a user selects the type of fluids to be warmed. The user can then input a setpoint within the range of temperatures using the user inputs 36.

The controller 30 is further configured to be replaceable, so that if the controller 30 fails, the controller 30 can be removed from the medical warming cabinet 10 and replaced with a new controller. The controller 30 can be configured to be replaceable through the use of removable connectors and lines that connect the controller 30 to the other components of the cabinet 10, such as a power supply, relays, the heating apparatus 15, and sensors. Because the removable memory device 16 can be removed from the controller 30 that is being replaced, the removable memory device 16 can be easily inserted into the new controller. Accordingly, the new controller is configured to operate exactly like the failed controller without having to tediously input the control parameters by using the user inputs and without requiring a specialized programming device. Furthermore, the controller 30 can be updated simply by removing an old removable storage device and either updating the old device or inserting a new removable memory device including the updated information. Once the new removable memory device is installed in the controller 30, the controller 30 loads the information, such as by loading a configuration file, from the removable memory device 16. In this way, the controller 30 can be also be easily updated.

For clarity, the removable memory device 16 is not the same as the external memory device that will be described below with respect to the data logging module. The removable memory device 16 is designed to be generally retained in the controller 30 during operation, except when, for example, replacing a faulty controller or upgrading the information for operation of the medical warming cabinet 10. As described above, replacement typically involves disassembly of the cabinet 10. In contrast, the external memory device is for offloading data from the cabinet 10, such as information that has been recorded pertaining to the operation of the cabinet 10. As will be described below, this periodic transferring of data is intended to be easy accessible by the user.

Figure 2:
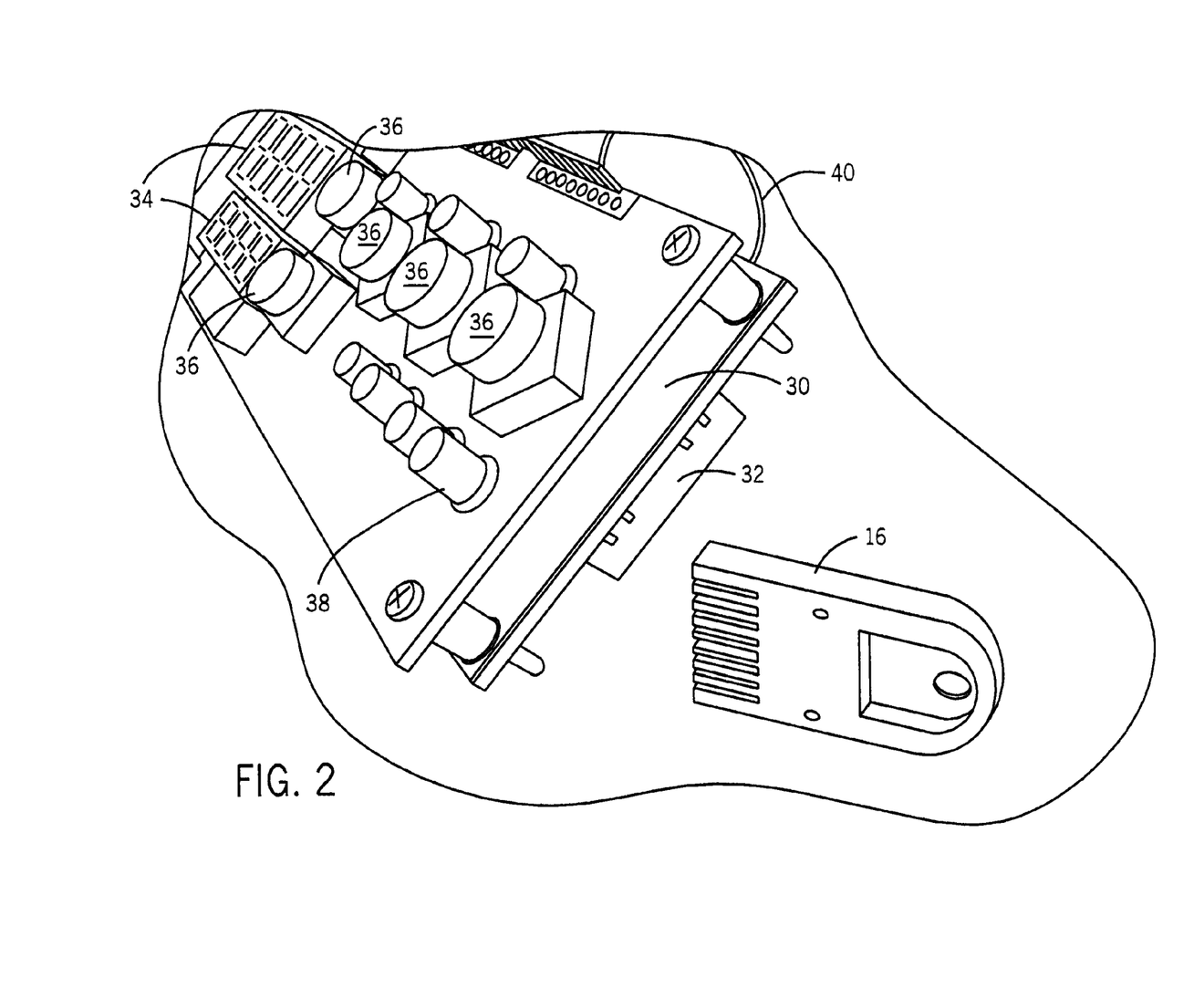
FIG. 2 is a perspective view of a medical warming cabinet controller with a removable memory device not yet inserted into a socket on the controller.
Figure 3:
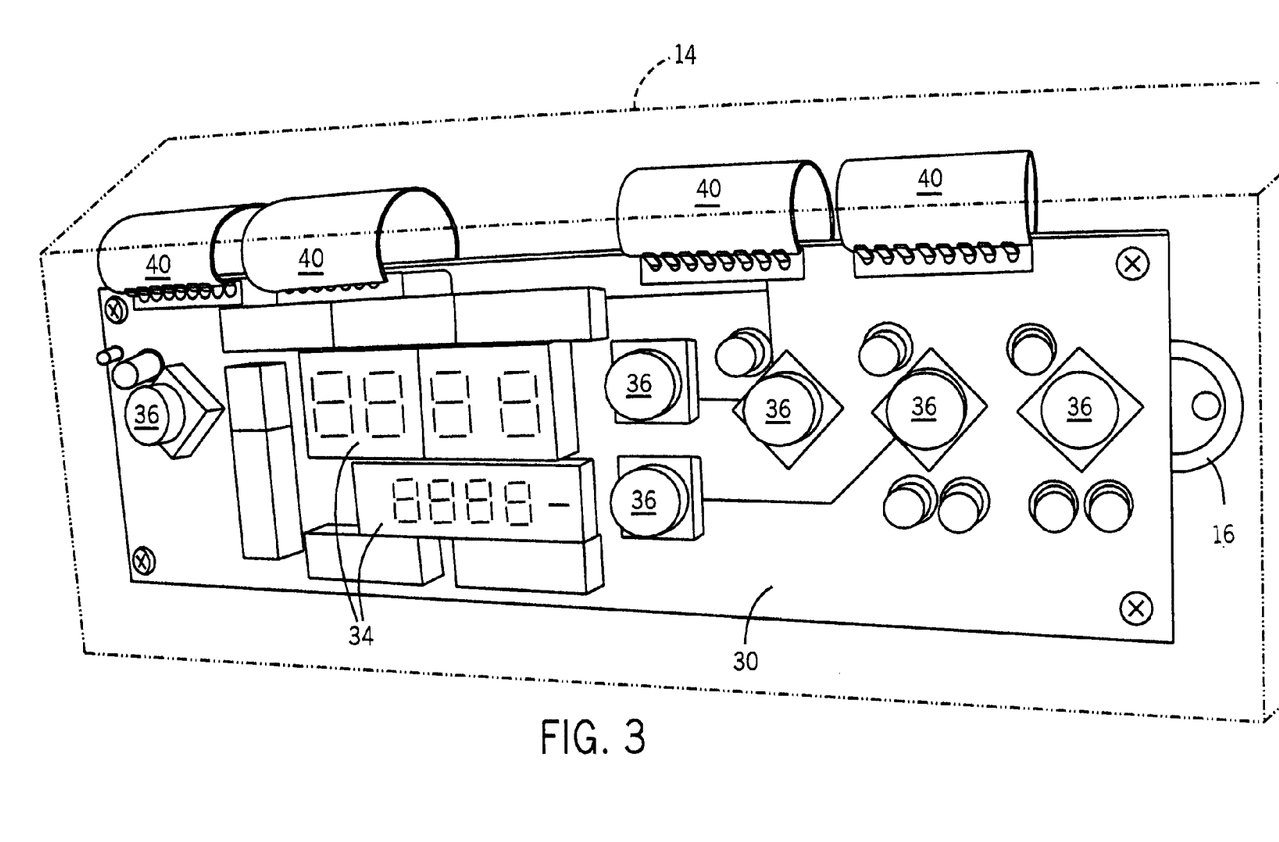
FIG. 3 is a perspective view of a medical warming cabinet controller with a removable memory device inserted into the socket.

FIGS. 2 and 3 show the controller 30 for use with a medical warming cabinet in further detail. The controller 30 includes a removable memory socket 32, the user display 34, the user inputs 36, LEDs 38, and a plurality of connectors 40 for connection to other components of a warming cabinet. In FIG. 2, the removable memory device 16 is shown removed from the removable memory socket 32. In FIG. 3, the removable memory device 16 is shown inserted into the removable memory socket 32, which can be a bus port. The removable memory device 16 can be a memory chip, memory stick, memory card, and the like. The removable memory socket 32 is configured to allow for the information stored on the removable memory device 16 to be loaded by controller 30. The controller 30 can comprise a plurality of printed circuit boards including a processor, memory, buses, communication lines, and other electrical components as is well understood in the art.

Figure 4:
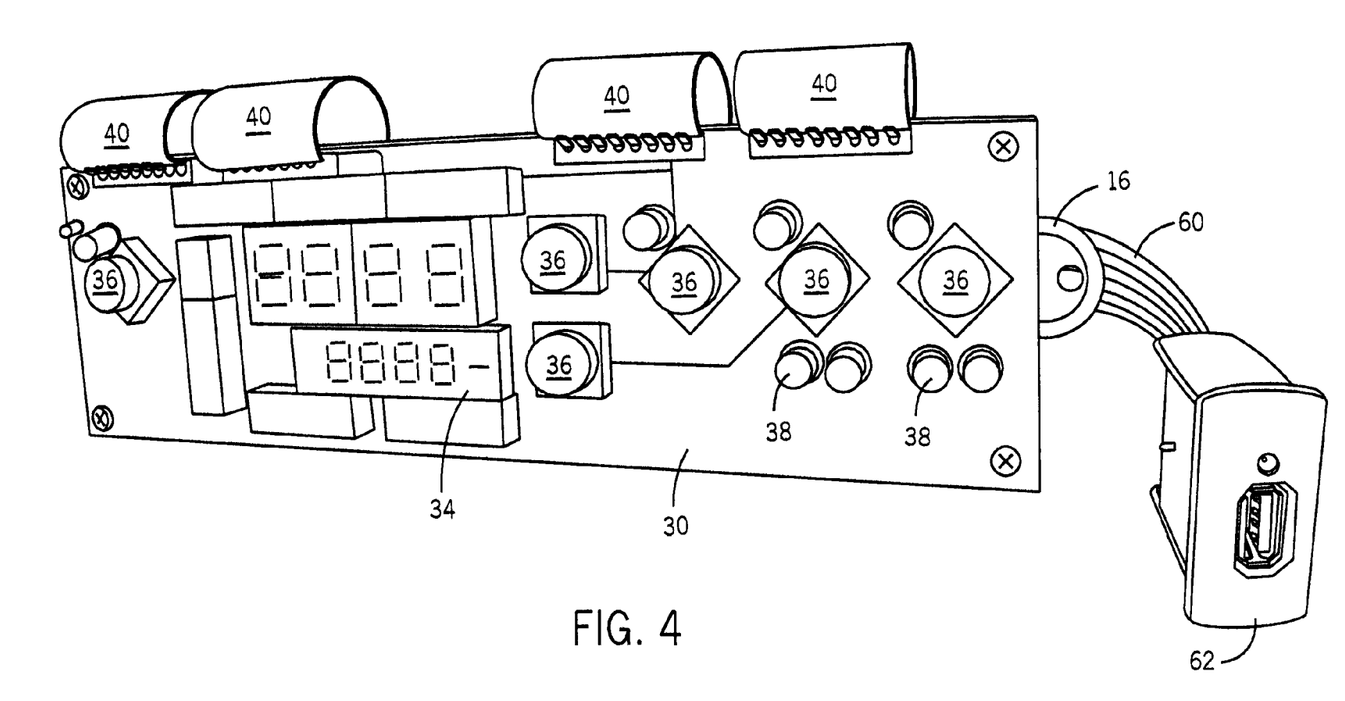
FIG. 4 is a perspective view of a medical warming device controller similar to FIG. 3, but in which the controller also has a bus port.

FIG. 4 shows a modified version of the controller 30 for use with a medical warming cabinet. As discussed in more detail below, the controller 30 includes a processor and memory device configured to operate as a data logging module. The memory device may be a portion of the removable memory device 16, memory onboard the controller 30, or any other type of memory storage. The controller 30 can comprise a plurality of printed circuit boards including a processor, memory, buses, communication lines, and other electrical components as is well understood in the art. The controller 30 is connected by bus lines 60 to a bus port 62, which is configured to receive a data logging memory device (not shown) that can be read/written by the controller 30. In one embodiment, the bus port 62 is a universal serial bus (USB) port and memory device is a USB flash drive. The bus port 62 is disposed on the medical warming cabinet 10 to be conveniently accessible without disassembling the medical warming cabinet 10 in which it is installed.

The data logging module of the controller 30 is configured to log (i.e., sample and record) operational data by sampling data at a predetermined sample rate and storing data packets for each sample. The data packets can include a time/date stamp, the current set point for the compartment 13, a first measured temperature of the compartment 13 provided by a first temperature sensor (such as temperature sensor 21), a second measured temperature of the compartment 13 provided by a second temperature sensor, a state of a door sensor 19 on the warmer, the warmer type, and error logging. All data sampling packets for temperature can be taken from the temperature sensor 21, but a preferred method is to have an additional sensor and circuitry for independent reporting of the warmer function. In an embodiment, the data packets are sampled at a rate of one per hour and are stored in a memory sized to store six months of data.

In one embodiment, the memory device is a circular memory buffer. As the operational information is sampled and recorded, the data packets are stored in the circular memory buffer and, when the memory is full, the oldest of the data packets are overwritten during the step of recording.

The controller 30 can be configured to use the display 34 to indicate that the data logging memory is full and a download is required or as the memory device is reaching capacity. In one embodiment, a message, such as the word "full", can flash alternately with a displayed temperature of the compartment. When a data logging memory device or external memory device is inserted into the bus port 62, the controller 30 automatically transfers the logged data to the data logging memory device. The controller 30 indicates on display 34 that the data is being downloaded to the data logging memory device and also indicates when the download has completed. In an embodiment, the display 34 shows "USB DMP" during the download and "USB DONE" once the download has completed and until the data logging memory device has been removed. Once the data logging memory device has been removed, the display function is returned to normal operation. The data can be written to the data logging memory device in a comma delimited format or summarized in a report having. In one embodiment, the user inputs 36 are not locked out when the data is being downloaded.

The controller 30 can be configured to summarize the logged data in a report format. The report format can be configured to exclude samples that were taken, for example, within two hours of when the door was open or, according to another example, within two hours of when the warmer was turned on. Of course, two hours is only one example and other lengths of time could be selected when determining which samples to exclude from the report. The report can be a text file including the following information: model number, serial number, date of manufacture of unit, date of report/download, software version, frequency a reading was taken, separate report sections for each set point, units, warmer mode, or month change of greater than eight valid readings, and an overall statement summarizing the accuracy of the data and indicating how the data was collected. The separate report section for each set point, units, warmer mode, or month change of greater than eight valid readings including the following information: period of accuracy the section covers, number of days the section covers, number of readings evaluated for the accuracy calculation, number of readings excluded from the accuracy calculation due to the door being opened within a specified time of a reading, mode of warming, warmer accuracy specification, warmer setpoint temperature, average temperature, temperature range, and accuracy evaluation statement indicating if the unit passed or failed to meet the specified accuracy at the selected set point.

In addition to the features described above, the controller 30 may incorporate other features. The controller 30 can be set by a user to operate in Fahrenheit and Celsius and allows a user to input a temperature within a range of temperatures. The controller 30 can include a timer that allows a user to control when the cabinet turns on and off. The controllers can also have a lock-out feature and a series of prompt sequence indicators. The controllers can also control interior lighting. The cabinet can include a warming shut-off system that is separate from controller and is configured to prevent overheating.

A warmer can include two compartments that are warmed separately, which allows for flexibility in choosing particular temperatures for warmed blankets or warmed fluids. Combination cabinets can include a blanket warming compartment and a fluid warming compartment. The compartments can be controlled by separate controllers. Alternatively, a single controller can be configured to control more than one compartment.

While there have been shown and described what is at present considered the preferred embodiments of the invention, it will be obvious to those skilled in the art that various changes and modifications can be made therein without departing from the scope of the invention defined by the appended claims.

What is claimed is:

1. A medical warming cabinet comprising:
   a compartment;
   a heating apparatus for warming the compartment;
   a controller configured to operate the heating apparatus, the controller including a removable memory device connector for receiving a removable memory device; and
   a removable memory device removably received in the removable memory device connector, the removable memory device containing information related to operational parameters specific to the medical warming cabinet;
   wherein the controller operates according to operational parameters stored on the removable memory device and wherein the removable memory device is configured to supply the operational parameters to the controller without requiring a user to manually input the operational parameters into the controllers
   wherein the removable memory device and the controller are configured to allow a user to replace the controller with a new controller by removing the removable memory device from the removable memory device connector of the controller, removing the controller from the medical warming cabinet, inserting their removable memory device into the removable memory device connector of the new controller, and installing the new controller into the medical warming cabinet, thereby transferring the operational parameters to the new controller.

2. The medical warming cabinet as in claim 1, wherein the controller includes user inputs for altering the information stored on the removable memory device.

3. The medical warming cabinet as in claim 1, further comprising a data logging module for sampling, storing, and reporting operational data.

4. The medical warming cabinet as in claim 1, wherein the medical warming cabinet includes at least a first compartment having a first heating apparatus and a second compartment having a second heating apparatus, the removable memory device containing separate operational parameters for the first compartment and the second compartment.

5. The medical warming cabinet as in claim 1, wherein the information includes heating control algorithm information.

6. The medical warming cabinet as in claim 1, wherein the removable memory device includes different operational parameters for different items to be warmed.

7. The medical warming cabinet as in claim 6, wherein the controller has individual temperature controls for irrigation fluids and injection fluids.

8. The medical warming cabinet as in claim 1, wherein the operational parameters include installation information specific to the medical warming cabinet.

9. A method of installing a controller into a medical warming cabinet comprising:
   providing a controller having a memory device connector and a connector for connecting the controller to a heating apparatus;
   providing a removable memory device containing information related to operational parameters specific to the medical warming cabinet;
   inserting the removable memory device into the memory device connector in the controller; and
   installing the controller into the medical warming cabinet;
   wherein the information on the removable memory device is read by the controller upon operation and the medical warming cabinet operates according to the information stored on the removable memory device, and wherein the removable memory device is configured to supply the operational parameters to the controller without requiring a user to manually input the operational parameters to the controller.

10. The method of claim 9, further comprising the step of operating user inputs on the controller to alter the information stored on the removable memory device.

11. The method of claim 9, further comprising sampling operational data using the controller and storing the operational data on a portion of the removable memory device.

12. The method of claim 9, wherein the medical warming cabinet includes at least a first compartment having a first heating apparatus and a second compartment having a second heating apparatus and wherein the information related to operational parameters of the medical warming cabinet includes separate operational parameters for the first compartment and the second compartment.

13. The method of claim 9, wherein the information includes heating control algorithm information.

14. The method of claim 9, wherein the removable memory device includes different operational parameters for different items to be warmed.

15. The method of claim 13, wherein the controller has individual temperature controls for irrigation fluids and injection fluids.

16. The method of installing a controller into a medical warming cabinet as in claim 9, further comprising the steps of:
   removing the removable memory device from the removable memory device connector in the controller upon failure of the controller;
   removing the controller from the medical warming cabinet;
   inserting the removable memory device into a removable memory device connector of a new controller; and
   installing the new controller into the medical warming cabinet, thereby transferring the operational parameters to the new controller.

17. The method of installing a controller into a medical warming cabinet as in claim 9, further comprising the steps of:
   removing the removable memory device from the removable memory device connector in the controller upon a need to update the controller;
   updating the removable memory device with updated operational parameters; and
   inserting the removable memory device back into the removable memory device connector, thereby transferring the updated operational parameters to the controller.

18. A medical warming cabinet comprising:
   a compartment;
   a heating apparatus for warming the compartment;
   a controller configured to operate the heating apparatus, the controller including a removable memory device connector for receiving a removable memory device; and
   a removable memory device removably received in the removable memory device connector, the removable memory device containing information related to operational parameters specific to the medical warming cabinet;
   wherein the controller operates according to operational parameters stored on the removable memory device and wherein the removable memory device is configured to supply the operational parameters to the controller without requiring a user to manually input the operational parameters into the controller wherein the removable memory device is configured to allow a user to update the controller by removing the removable memory device from the removable memory device connector, updating the movable memory device with updated operational parameters, and inserting the removable device back into the removable memory device connector, thereby transferring the updated operational parameters to the controller.

19. The method of claim 18, further comprising the step of operating user inputs on the controller to alter the information stored on the removable memory device.

20. The medical warming cabinet as in claim 18, wherein the removable memory device includes different operational parameters for different items to be warmed.

21. The medical warming cabinet as in claim 20, wherein the controller has individual temperature controls for irrigation fluids and injection fluids.

\* \* \* \* \*